United States Patent
Moshe et al.

(10) Patent No.: US 6,476,619 B1
(45) Date of Patent: Nov. 5, 2002

(54) METHOD AND DEVICE FOR HIGHLY ACCURATE, HIGH SPEED, REAL TIME, CONTINUOUS OR STATIONARY, IN-LINE, NON-INVASIVE, THREE DIMENSIONAL, MULTI-SLICE AND CALCULATIONS OF HOMOGENEOUS OR NON-HOMOGENEOUS FIBROUS YARN, SLIVERS, OR PAD MATERIAL

(75) Inventors: Danny S. Moshe, Kiryat Ono (IL); Alexander Greenwald, Nazirith Illit (IL); Leonid M. Buzik, Haifa (IL)

(73) Assignee: Malcam Ltd., Tel Aviv (IL)

( * ) Notice: Subject to any disclaimer, the term of this patent is extended or adjusted under 35 U.S.C. 154(b) by 41 days.

(21) Appl. No.: 09/640,973

(22) Filed: Aug. 17, 2000

Related U.S. Application Data (63) Continuation of application No. 09/143,966, filed on Aug. 31, 1998, now abandoned.

(51) Int. Cl.[7] .............................................. G01R 27/32
(52) U.S. Cl. ..................... 324/634; 324/636; 324/640
(58) Field of Search ................................ 324/634, 635, 324/636, 640, 639, 664; 73/32 R (56) References Cited

U.S. PATENT DOCUMENTS

| | | | | |
|---|---|---|---|---|
| 3,559,043 A | | 1/1971 | Hyde | 324/316 |
| 4,211,970 A | * | 7/1980 | Fitsky et al. | 324/634 |
| 4,297,874 A | * | 11/1981 | Sasaki | 73/73 |
| 4,885,527 A | * | 12/1989 | Lacombe et al. | 324/636 |
| 4,890,054 A | | 12/1989 | Maeno et al. | 324/640 |
| 5,057,781 A | * | 10/1991 | Atkins et al. | 324/635 |
| 5,397,993 A | * | 3/1995 | Tews et al. | 324/624 |
| 5,977,780 A | * | 11/1999 | Herrmann | 324/640 |
| 6,184,694 B1 | * | 2/2001 | Anderson et al. | 324/635 |

OTHER PUBLICATIONS

"Draft Guidance For The Content of Premarker Notifications for Menstrual Tampons", Obstetrics–Gynecology Devices Branch, Office of Device Evaluation, Center for Devices and Radiological Health, May 25, 1995.

Kraszewski, A W, "Microwave Aquametry–Needs and Perpectives", *IEEE Trans. On Microwave Theory and Techniques*, 39(5): 828, 833, 1991.

\* cited by examiner

Primary Examiner—N. Le
Assistant Examiner—Walter Benson
(74) *Attorney, Agent, or Firm*—G.E. Ehrlich Ltd.

(57) ABSTRACT

A method for highly accurate, high speed, multi-slice density and moisture content measurements and calculations of homogeneous or non-homogeneous fibrous material, using a microwave resonator device and computer algorithms. The device is comprised of a cylindrical microwave resonator, including two cutoff waveguides, internal corrective pieces, a teflon tube, signal input and output ports, alternative microwave sources, alternative signal receivers, temperature sensor and optional moisture sensor, and computerized processing and display units. The method comprises passing fibrous material, located in-line of a production process, through the resonator, wherein the fibrous material is scanned with a sweeping range of microwave frequencies, in a continuous, real time, and multi-slice mode. The presence of the fibrous material causes resonance frequency shifts and changes in resonator quality, which are proportional to, and used in calculations of, material density and moisture content, respectively. Calculations of material density (and moisture content) are based on evaluation of density and moisture content arrays (of time samples), which are functions of resonator frequency shift and quality data, empirically determined density, moisture content, and structurally dependent correlation functions, and material temperature. Improved accuracy in values of density is obtained by compensating for moisture content. Density and moisture content values are used for real time quality control feedback of process parameters, including fiber density, moisture content, temperature, and incoming feed rate.

40 Claims, 8 Drawing Sheets

METHOD AND DEVICE FOR HIGHLY ACCURATE, HIGH SPEED, REAL TIME, CONTINUOUS OR STATIONARY, IN-LINE, NON-INVASIVE, THREE DIMENSIONAL, MULTI-SLICE AND CALCULATIONS OF HOMOGENEOUS OR NON-HOMOGENEOUS FIBROUS YARN, SLIVERS, OR PAD MATERIAL

This is a Continuation of pending U.S. patent application Ser. No. 09/143,966, filed Aug. 31, 1998 and now abandoned.

FIELD AND BACKGROUND OF THE INVENTION

The present invention relates to density measurements of fibrous materials. In particular, this invention relates to a method and device for determining high-speed, real-time, continuous or stationary, in-line, non-invasive, three dimensional multi-point density deviation and density measurements and calculations of yarn, slivers, or pads of non-homogeneous fibrous material, used in the manufacture of feminine hygiene products (i.e., menstrual tampons, pads, and panty liners), as an example, and other fiber based products.

The manufacture of menstrual tampon products is based on the processing of yarn, slivers, or pads of non-homogeneous fibrous material, consisting of some combination of cotton and synthetic and/or cellulosic fibers. Fiber density and moisture content typically vary during the manufacturing process, primarily due to variation in fiber composition. Combining and controlling the proper relative amounts of cotton and synthetic and/or cellulosic fibers in a given tampon manufacturing production line can be accomplished by incorporating high-speed accurate measurement and control of in-line fiber density, moisture content, and temperature.

The main component of tampons is cotton, with synthetic (e.g., viscose rayon, rayon polyacrylates, polyester) and/or cellulosic (e.g., carboxymethol-cellulose) fibers mixed with the cotton to substantially increase the absorbency and anti-wicking properties of tampons. Since the late 1980's, it has been established through widespread investigation and research, court proceedings (e.g., United States District Court For The District Of Kansas, Case No. 94-1195-FGT), FDA reports and guidelines (e.g., Draft Guidance For The Content Of Pre-market Notifications For Menstrual Tampons, Obstetrics-Gynecology Devices Branch, Office Of Device Evaluation, Center For Devices And Radiological Health, May 25, 1995), that synthetic fibers in tampons are associated with Toxic Shock Syndrome (TSS) and infection in menstrual women. In the case of TSS, the presence of synthetic fibers in tampons has been determined to cause an increase in the production of toxic chemicals in the woman's body. In the case of infection, the presence of synthetic fibers in tampons inhibits the growth or existence of vaginal flora, due to excessive absorbency of vaginal moisture, necessary for proper vaginal health. Additionally, there are reports that synthetic fibers themselves contain toxins (e.g., "The Health Risks of Dioxin", an FDA scientist's report referenced by U.S. congressman Rep. Ted Weiss, at a hearing of the Human and Intergovernmental Relations Subcommittee, Jun. 10, 1992). At that hearing, the FDA concluded that there was dioxin in rayon, and stated that if they (the FDA) did have a problem with medical devices, "menstrual products would be the greatest simply because of the mass of the material and the duration of exposure". Thus, the potential of tampons causing TSS or infection is directly related to the synthetic fiber content, which in turn, is related to the overall tampon raw material fiber density and moisture content. From this background and information, it is apparent that accurate measure and control of density and moisture content during the manufacture of tampons is important not only from a manufacturing quality control viewpoint, but, also, from a health issue viewpoint.

In the manufacture of products containing fibrous yarn, sliver, or pad raw material, it is desirable to use the fiber density as a primary control parameter, especially in real time, in-line, and continuous mode of operation, in order to maintain product quality assurance (i.e., product composition and performance reproducibility). For a given composition of yarn, sliver, or pad material, fiber density is dependent on its moisture content, and to a lesser extent, dependent upon its temperature. Real time, in-line quality control of the fiber content, of finished feminine hygiene products, for example, is best achieved by measuring and calculating density and moisture deviations and controlling the density and moisture content of the fibrous raw material at both upstream and downstream stages of the manufacturing process.

Prior art devices and methods for measuring fiber density and moisture content are primarily mechanically based, suited for stationary, off-line, and invasive or direct contact operation and analysis of bulk quantities of materials with relatively high densities. Techniques utilizing radiation have been used for density and moisture measurements. Infra-red techniques can be used for moisture determination, but these require direct contact with the material, and are affected by the presence of industrial dust and the focal plane immediately around the sample; Beta rays have been used for density determination, but here there is a health hazard limitation in its application at manufacturing sites. Microwave and other electrical devices and methods for measuring density deviations and density of fibrous materials via moisture and temperature measurements discussed by Kraszewski, A. W. (Microwave Aquametry-Needs and Perspectives, IEEE Transactions On Microwave Theory And Techniques, vol. 39, no. 5, May 1991), provides background and discusses the development of microwave equipment for purposes of electrical monitoring of moisture content in materials. Included there are useful basic definitions, principles, and equations pertaining to microwave analysis of moisture content in materials. At specified material temperature, changes in attenuation and phase-shifts of transmitted microwaves are used for calculating material moisture and density values, respectively.

U.S. patent application Ser. No. 08/974,983, and now U.S. Pat. No. 6,025,724 and Ser. No. 08/777,872, and now U.S. Pat. No. 5,845,529 describe microwave based devices and methods for determining the moisture content of packaged, and non-packaged material, respectively, utilizing various antenna configurations as the source and receiver of transmitted microwave radiation. The earlier of this pair of related patent applications, U.S. patent application Ser. No. 08/777,872, describes moisture content determination of a given module of material (e.g., cotton, paper, processed wood, tea, synthetic fibers). The moisture measuring equipment is aimed at monitoring upstream incoming raw fibrous material, i.e., prior to fibrous material entering the CARD (i.e., fiber separating and processing) machine, and represents a 'coarse' monitoring and analysis of moisture content of upstream incoming fibrous material. As such, the invention is essentially limited to measurement of relatively large (bulk) quantities of minimally processed, high density fibrous material (e.g., typically, 10–15 kilograms per cubic meter), and not highly processed, low density fibrous material (e.g., typically, 4–12 grams per meter, linear density) composed of loose fibers, such as yarn, slivers, or pads (e.g., for tampon production). Moisture content is determined as a function of changes in signal attenuation (amplitude). Compensation of the phase shift for moisture and temperature change is not shown, and there is no discussion pertaining to density deviation measurement or calculation.

U.S. patent application Ser. No. 08/974,983, builds on U.S. patent application Ser. No. 08/777,872, in that compensation for temperature changes of the material, and a method for measurement and calculation of density deviations of indicated material, are included in the invention. A similar, microwave based, dual antenna device is used; phase-shifts and signal attenuation measurements, are used for calculating density and moisture content, respectively. An algorithm was developed to process and maintain the numerical information and data. This invention, too, is essentially limited to measurements of relatively large (bulk) quantities of minimally processed, high density material, and not highly processed, small density fibrous material composed of loose fibers, such as yarn, slivers, or pads. Moreover this invention is specific to providing the method and device of moisture content determination of material wound around a bobbin containing a hollow core. Of these two related patent applications, the more recent one (i.e., U.S. patent application Ser. No. 08/974,983) briefly mentions a form of quality control adjustment of the moisture content of the material, which includes moisture monitoring equipment appropriate for location at an upstream, 'coarse', stage of the fiber based manufacturing process (i.e., pre-CARD fiber separating and processing machine), which can be electronically connected to, and controlled by a central processing unit.

There is thus a widely recognized need for, and it would be highly advantageous to have a highly accurate, high speed, real time, continuous or stationary, in-line, non-invasive, three dimensional, multi-slice method and device for measuring and calculating (small) density deviations, and (low) densities of homogeneous or non-homogeneous fibrous material, at a downstream (fine) stage of production, which includes the capability of compensation for material moisture content and temperature changes, with the object of providing highly accurate, high speed, real-time, continuous or stationary, in-line, non-invasive computerized quality control feedback of critical manufacturing process parameters involved in the production of high quality and high assurance fiber based products (e.g., feminine hygiene products, including menstrual tampons as just one example).

SUMMARY OF THE INVENTION

The present invention includes a method and device for highly accurate, high speed, real time, continuous or stationary, in-line, non-invasive, three dimensional, multi-slice density deviation and density measurements and calculations of homogeneous or non-homogeneous fibrous yarn, slivers, or pad material.

The method and device of the present invention enables measurement and calculation of small density deviations and low densities of homogeneous or non-homogeneous fibrous yarn, slivers, or pad material.

The method and device of the present invention also enables highly accurate, high speed, real time, continuous or stationary, in-line, non-invasive computerized quality control feedback of critical manufacturing process parameters involved in the production of high quality and high assurance fiber based (including low density) products.

According to the present invention, there is provided a method for determining the density of a fibrous material, including the steps of (a) introducing the fibrous material into a resonator having a resonance frequency, (b) measuring a shift in the resonance frequency caused by the fibrous material, and (c) inferring the density of the fibrous material from the frequency shift.

According to the present invention, there is provided a device for determining the density of fibrous material, including: (a) a resonator, including an electrically conductive housing defining a cavity, having an input end and an output end, the resonator having a resonance frequency; (b) a tube of low-friction material spanning the cavity from the input end to the output end; and (c) a mechanism for measuring a shift in the resonance frequency caused by the presence of the fibrous material inside the cavity.

According to the present invention, there is provided a device for determining the density of fibrous material, including: (a) a resonator, including: (i) an electrically conductive housing, defining a symmetrical cavity having two substantially identical resonance frequencies with respect to two degenerate modes of microwave radiation, and (ii) a mechanism for perturbing the symmetry, so that the resonator has two distinct resonance frequencies with respect to the two degenerate modes; and (b) a mechanism for measuring a shift in one of the distinct resonance frequencies caused by a presence of the fibrous material inside the cavity.

According to the present invention, there is provided a system for processing fibrous material, including: (a) a CARD machine for separating the fibrous material and reducing the density of the fibrous material; and (b) a mechanism for measuring the density of the fibrous material emerging from the CARD machine, the mechanism including a resonator where through the fibrous material passes.

According to the present invention, there is provided a method for determining highly accurate density profiles of fibrous material used in the manufacture of tampons, leading to improved controllability and quality of the density of the fibrous material, including the steps of: (a) introducing the fibrous material into a resonator having a resonance frequency; (b) measuring a shift in the resonance frequency caused by the fibrous material; and (c) inferring the density of the fibrous material from the shift.

According to the present invention, there is provided a method for determining highly accurate moisture content profiles of fibrous material used in the manufacture of tampons, leading to improved controllability and quality of the moisture content of the fibrous material, including the steps of: (a) introducing the fibrous material into a resonator having a resonator quality; (b) measuring a change in the resonator quality caused by the fibrous material; and (c) inferring the moisture content of the fibrous material from the change in resonator quality.

According to the present invention, there is provided a method for determining highly accurate density profiles of fibrous slivers, leading to improved controllability and quality of the density of the fibrous slivers, including the steps of: (a) introducing the fibrous slivers into a resonator having a resonance frequency; (b) measuring a shift in the resonance frequency caused by the fibrous slivers; and (c) inferring the density of the fibrous slivers from the shift.

According to the present invention, there is provided a method for determining highly accurate moisture content profiles of fibrous slivers, leading to improved controllability and quality of the moisture content of the fibrous slivers, including the steps of: (a) introducing the fibrous slivers into a resonator having a resonator quality; (b) measuring a change in the resonator quality caused by the fibrous slivers; and (c) inferring the moisture content of the fibrous slivers from the change in resonator quality.

The preferred embodiment of the present invention employs a microwave radiation measuring device which operates as a high speed (i.e., micro- to milli-second turn-around-time for measurement, analysis, and processing of each datapoint), multi-slicing (i.e., in-line, continuous mode of operation such that analysis is continuously performed on small, of the order of 2 mm slices of the fibrous material), highly accurate, microwave resonator of non-specific geometry (e.g., cylindrical, coaxial, rectangular), including alternative methods of generating microwave radiation inside the resonator, two cutoff waveguides, a teflon tube for material transport inside the resonator, and components as part of and inside the resonator to correct for imperfections, asymmetry and/or non-homogeneities of the resonator and/or waveguides materials of construction.

The microwave resonator device can operate in at least two alternative modes, including embodiment (a) where the microwave radiation is generated by a broadband microwave generator-synthesizer, and embodiment (b) where the microwave radiation is generated in an oscillator circuit comprising the resonator device (with fibrous material inside of it providing capacitance), and an amplifier with DC power supply. The microwave resonator device in each embodiment is preferably operated for the generation and measurement of resonator resonance frequency shifts (i.e., changes in $f_r$, where $f_r$ represents resonator resonance frequency associated with, and measured at, microwaves having maximum amplitude, $A_m$), due to density changes of the analyzed fibrous material.

The device operating in embodiment (a) includes a generator-synthesizer continuously generating a sweeping range of frequencies, controlled by the central processing unit, such that corresponding continuous detection is aimed at identifying microwaves of maximum amplitude, enabling measurement and processing of an array of resonator resonance frequencies, $f_r$. Moreover, due to the electronic set-up of embodiment (a), measurement and processing of a second array is possible, i.e., resonator quality, Q, where $Q=f_r/(2\Delta f$, and $\Delta f$ represents the full width half amplitude bandwidth, evaluated at half-height of the microwave with maximum amplitude, $A_m/2$. In embodiment (a), values of resonator quality, Q, are used as part of a computerized and automatic method for determining moisture content of the fibrous material, which in turn are used to compensate and correct initial calculations of density deviation and density performed by the computer algorithm using resonance frequency shift data. For the device operating as embodiment (a), a separate external moisture content sensor is not needed as part of the overall device of the present invention.

For the device operating in alternative embodiment (b), resonator quality, Q, is not measured, because of the different electronic set-up of the microwave resonator circuit; as such, a separate external moisture content sensor is optionally added to the overall resonator device, thus, enabling compensation and correction of measurements and calculations of density deviation and density by the computer algorithm. For each embodiment, the microwave resonator method and device have the optional capability of measuring and evaluating changes in temperature of the fibrous material, including the addition of a separate external temperature sensor as part of the overall resonator device. Each embodiment of the microwave resonator device has the additional optional capability of providing automatic quality control feedback of critical manufacturing process parameters of the fiber material, including fiber density, moisture content, temperature, and feed rate, at a downstream (fine tune) stage of the overall manufacturing process. For the device operating in embodiment (a), additional components including a heterodyne generator-synthesizer and a signal mixer may be added to the same circuit of the microwave resonator device, in order to provide additional dynamic range, improved sensitivity and accuracy in signal detection, and subsequent enhancement of feedback information sent to the upstream incoming fibrous material processing equipment.

The high speed (i.e., micro- to milli- second turn-around-time for measurement, analysis, calculation, and processing of each data point), multi-slice microwave resonator method and device, including optional capabilities of temperature and moisture content sensors for measurement and calculation, and automatic quality control feedback, are controlled by an in-line central processing unit. The central processing unit contains specially developed algorithms for performing data reduction and calculations from measurements of multi-slice analysis of fibrous materials, based on measurements of the affected microwaves inside the microwave resonator device, including the conversion of frequency shift, resonator quality, and voltage measurements into density deviation, average density, moisture content, and temperature. Values of density deviation and average density, and optionally, moisture content and/or temperature, as functions of time, are numerically and/or graphically displayed on an in-line computerized display unit. The combination of the central processing unit, which includes electronic components for (A/D) digital signal processing, and a computerized display unit, provides a variety of electronic storage and manipulation, including hardcopy printouts of desired measurements, calculations, numerical data and/or graphs.

The computer algorithm, especially written for multi-slice (i.e., of the fibrous material) data reduction, calculations of the various measurements, and generating values of density deviation, average density, and optionally, moisture content, is preferably (i.e., as in embodiment (a)) based on two principle arrays: 1) microwave resonator resonance frequency, $f_r$, and 2) signal (resonator) quality, Q. Material density and moisture content are directly proportional to these arrays, respectively, whereby appropriate functions and equations are used for performing the necessary calculations. Actual values of fiber material density, used for in-line processing purposes, are evaluated, in part, from empirical functions, data of which is contained in calibration graphs of resonance frequency, $f_r$, vs density, and resonator quality, Q, vs density, for a variety of fibrous materials at known temperature and moisture content, recorded under off-line, controlled calibration conditions. In embodiment (a), improved accuracy in final density calculations is gained, if desired, by compensating initial calculations of the density for material moisture content, material structure (i.e., shape, type), and temperature. Moisture content is evaluated from measurements and calculations of resonator quality; functions of material structure are evaluated from employing the resonator device at standard conditions, and for various well characterized shapes and types of fibers; and temperature is evaluated from an appropriately located external temperature sensor near the entrance to the resonator device.

For embodiment (b), multi-slice data reduction, calculations of the various measurements, and generating values of density deviation, average density, and optionally, moisture content, is based on one principle array, i.e., microwave resonator resonance frequency, $f_r$. As in embodiment (a), material density is directly proportional to this array, whereby appropriate functions and equations are used for performing the necessary calculations. Actual values of fiber material density are evaluated, in part, from empirical functions, data of which is contained in calibration graphs of resonance frequency, $f_r$, vs density, for a variety of fibrous materials at known temperature and moisture content, recorded under off-line, controlled calibration conditions. In this embodiment, improved accuracy in final density calculations is gained, if desired, by compensating initial calculations of the density for material moisture content, material structure (i.e., shape and type), and temperature. However, in this embodiment, values of moisture content are obtained from actual measurements, taken from an optional externally located moisture content sensor. Final, compensated values of material density, as in embodiment (a), require the use of empirical functions of material structure, and temperature, where material temperature is evaluated from the external temperature sensor located near the entrance to the resonator device.

Physical location of the microwave resonator device with respect to the overall fiber based manufacturing process is between equipment used for upstream (coarse) handling and processing of incoming raw fibrous material, including a CARD fiber separating machine, and downstream (fine) processing equipment involved in further processing the separated fibrous material into finished products. Information provided by the microwave resonator device to the central processing unit represents 'fine tuning' capability of fiber processing parameters critical to downstream stages of the overall production process, whereas, moisture/density monitoring equipment situated upstream of the fiber separating CARD machine represents 'coarse tuning' capability of fiber processing parameters critical to fibrous material entering the CARD machine, and serves as an 'alarm' of large, erratic, or otherwise undesirable density deviations occurring early in the production process. Location of the resonator device of this invention is well suited for high speed, in-line quality control feedback of various incoming raw fibrous material characteristics, including density, moisture content, and temperature; and process parameters, including incoming material feed rate, and momentum of the CARD machine cylinders.

The embodiments of the present invention allow the capability of design modification according to the exact type of application, depending upon such factors as type, size, and density of the fibrous material, as well as the exact nature of the overall manufacturing process of a particular fiber based finished product.

Novelty and advantage of the present invention over prior art devices and methods for density measurement of fibrous material is based on its ability to monitor, measure, and calculate in real time (i.e., synchronization between all device components), density (and optionally, moisture content and orientation of the fibrous material) deviations in continuous or stationary, in-line, and non-invasive mode of operation with high accuracy and high speed. Moreover, the method and device are applicable to three dimensional, multi-slice measurement and analysis of fibrous materials. In order to emphasis the advantage of the ability of the device in the present invention to perform real time, multi-slice analysis, an actual 'working' illustration of this device follows: For a typical, continuous mode of operation, fibrous pad speed of 1200 meter/min=20 meter/sec=20 millimeter/millisecond, this device is capable of measuring, recording, and processing measurements at a rate of one datapoint (i.e., one slice) every 0.1 millisecond; thus, each recorded data point (slice) represents 2.0 mm of fibrous pad material, being supplied during the manufacture of tampon products. Turnaround data processing time, i.e., time from initial measurement to the time of feedback control action, and sample size provided here as an example, give an idea of the rapidity and accuracy the quality control feedback loop this device is capable of during actual manufacturing of tampons, for example, and other textile products.

Another important advantage of the method and device of the present invention, absent from the prior art, is its applicability to measurement and analysis of small density deviations and to low (linear) density fibrous materials, such as yarn, slivers (e.g., 4–5 grams per meter) and pad (e.g., 11–12 grams per meter), used in the manufacture of tampons. Preferred location of the resonator device of the present invention is at a strategic point of fine adjust to the overall manufacturing process, i.e., downstream from the CARD fiber separating and processing machine.

Another advantage of the present invention is that density measurements are corrected for moisture content, and temperature changes of the fibrous material, during real time, continuous or stationary, in-line, non-invasive, three dimensional, and multi-slice mode of operation.

An additional novelty of the present invention is its ability to likewise, provide automatic quality control feedback. A practical example of the utility of the automatic quality control feedback during the manufacturing process occurs when feedback control triggers automatic adjustment of process parameters such as a) incoming raw material feed rate, b) momentum of fiber processing equipment cylinders (i.e., of the CARD machine), and c) raw material humidity and air temperature, enabling better control of moisture level and ultimately density of the finished fiber based product. Moreover, the device of the present invention is advantageously used in a complementary way to devices of prior art, in that the resonator device of this invention is preferably used for fine tuning quality control, whereas, microwave monitoring devices of above referenced patent applications are preferably used for coarse tuning quality control, with respect to a given overall fiber based manufacturing process.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a method and device which can be used for highly accurate, high speed, real-time, continuous or stationary, in-line, non-invasive, three dimensional multi-slice measurements of density deviations of homogeneous or non-homogeneous fibrous yarn, sliver, or pad materials, e.g., for the manufacture of tampons), or other fiber based textile products.

The principles and operation of the method and device according to the present invention may be better understood with reference to the drawings and the accompanying description.

Figure 1:
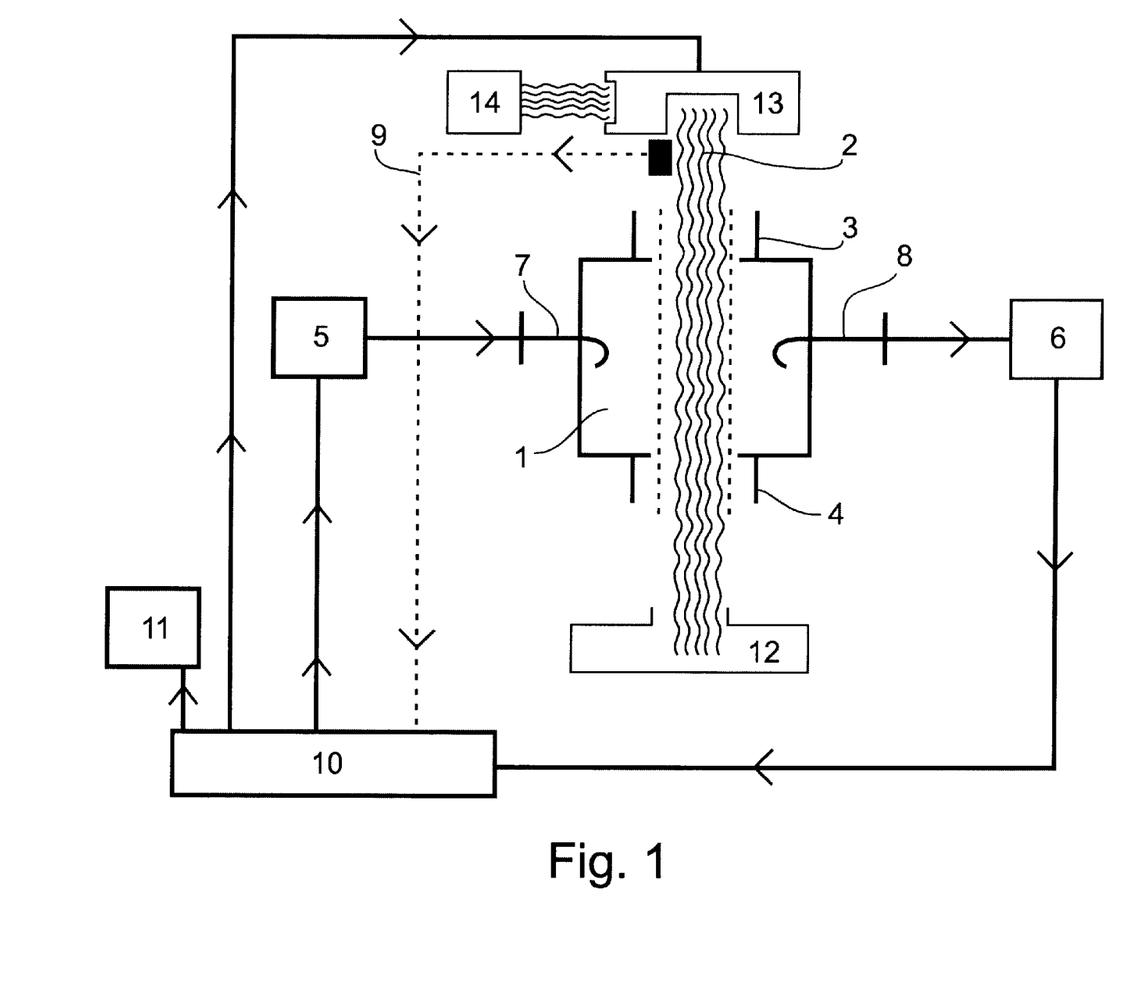
FIG. 1 is a schematic of one embodiment, (a), of the present invention, based on the microwave/waveguide resonator device operated with a microwave generator-synthesizer.

Referring now to the drawings, FIG. 1 is a schematic diagram of one embodiment, (a), of the basic device for performing the density measurements of the present invention. It is to be noted that this device is given for illustrative purposes only and is not meant to be limiting. During typical operation (production or calibration; continuous or stationary mode), fibrous material 2, for the primary application of this invention, is a continuously moving or stationary fibrous yarn, sliver, or pad, to be the object of real-time, in-line, non-invasive, multi-slice analysis and quality control of its density deviation and density, and optionally, moisture content, temperature, and other process parameters. Material 2 is positioned (not necessarily symmetrically) inside the hollow portion (i.e., cavity), of, and is surrounded by, a cylindrical microwave resonator/waveguide device 1. Microwaves of controllable, specified frequencies (e.g., typical working range of 7–8 GHz, for sliver, and 3.5–4.5 GHz, for pad, fibrous material; with an applicable range of 2–10 GHz) are generated by a microwave radiation broadband generator-synthesizer 5. The broadband generator-synthesizer 5 continuously generates, in a sweeping mode, microwave radiation of frequencies within pre-set ranges, and feeds the microwaves through microwave input port 7, into the microwave resonator/waveguide device 1. Two cutoff waveguides 3 and 4 (as part of, or as separately attached pieces) extending from the top and bottom of the microwave/waveguide resonator 1 are used to contain the microwave radiation inside the resonator, thereby maintaining high quality, Q, of the resonator (i.e., of the microwave signals inside the resonator). The cutoff waveguides 3 and 4 also assist in guiding material 2 through the microwave resonator device 1 during measurement.

The sweeping range of microwave frequencies impinges upon fibrous material 2 such that it becomes a set of perturbed microwaves. The perturbed microwaves are continuously received by and further transmitted through microwave output port 8, into signal receiver 6. From signal receiver 6, the microwave signals go to the central processing unit (CPU) 10, simultaneous to continuously received values of material temperature received from a strategically located external temperature sensor 9. The central processing unit 10 contains specially written algorithms which utilize stored resonator resonance frequency shift data, along with stored data contained in empirically determined calibration graphs of fiber material density vs resonator resonance frequency (obtained from off-line calibration measurements of standard fibrous materials under controlled conditions). Additional information generated by these algorithms includes values of material moisture content, calculated from measurements of resonator quality, Q, and from stored data contained in empirically determined calibration graphs of fiber moisture content vs resonator quality (similarly obtained from off-line calibration measurements of standard fibrous materials under controlled conditions). Data of material moisture content, and material temperature, are optionally used by the algorithms in the CPU 10 to compensate initial calculations of, and to improve the accuracy of, reported density deviation and density. Values of density, and optionally, other selected material characteristics, including moisture content and temperature, obtained from the above (i.e., A/D) signal processing performed by the CPU 10, are displayed, in real time and continuous mode, numerically and/or graphically, on the computerized display unit 11. These values provide the overall manufacturing process the capability of real time, continuous mode, in-line, non-invasive automatic quality control feedback of incoming (i.e., post-CARD machine) fibrous material density, via measurement, control and adjustment of incoming material moisture content, temperature, and feed rate. Quality control feedback and adjustment are automatically performed having electronic connection between the CPU 10 and the CARD machine 13. Synchronization is maintained among the microwave generator-synthesizer 5, microwave/waveguide resonator 1, signal receiver 6, CPU 10, display unit 11, temperature sensor 9, and the CARD machine 13, thus forming an automated quality control feedback loop.

Embodiment (a) in FIG. 1 also illustrates typical material input and output components in relation to the location of the device of the present invention. Unprocessed, relatively high density (e.g., 10–15 kg per cubic meter), fibrous raw material 14 is fed into the CARD machine 13. The CARD machine functions to separate and decrease the density of fibers at an upstream stage, in order to enable the programmed mixing of the fibers at a downstream production stage. Fibrous material exiting the CARD machine 13, is in the form lower density (e.g., 4–12 grams per meter, linear density) of yarn, slivers, or pad, and enters the in-line microwave/waveguide resonator device 1. Fibrous material exiting the microwave/waveguide resonator device 1 continues into a further downstream fiber processing machine 12, en route to finished fiber based product. This location of the microwave resonator device 1 is well suited, in a complementary way, to serve as part of fine tune control of semi-processed fibrous material, relative to the upstream location of an optional moisture content monitor (coarse control) of unprocessed fibrous raw material.

Figure 2A:
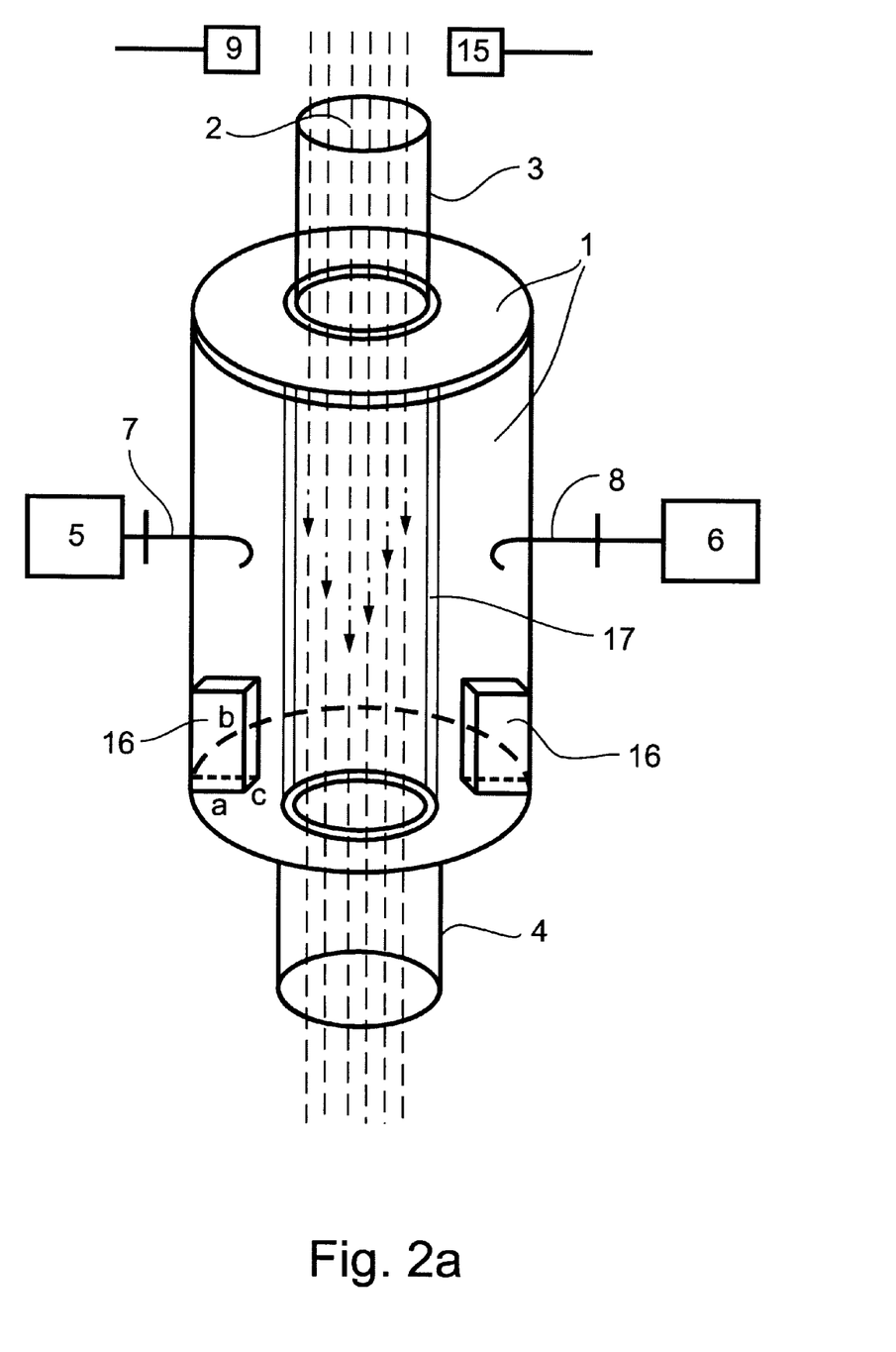
FIG. 2a is a close-up schematic of the cylindrical microwave resonator/waveguide device included and shown in FIG. 1.

FIG. 2a shows a close-up of the cylindrical microwave/ waveguide resonator device 1 with fibrous yarn, sliver, or pad material 2 in the hollow portion, or cavity. This embodiment illustrates and describes, but is not limited to, a cylindrical microwave resonator. The cylindrical microwave resonator 1 includes a hollow piece of cylindrically shaped metal, having typical dimensions of 44 mm height and 38 mm diameter, and is composed of high purity copper, silver, gold, or invar alloy. The entire inner surface of the cylindrical microwave resonator 1 is anodized with high purity gold or silver. Gold or silver is selected as the anodizing metal for their superior conductivity and anti-corrosive properties compared to base metals, such as copper or invar. This anodized metal design enhances resonator performance and quality characteristics.

Cylindrical cutoff waveguides (including base plates) 3 and 4, (preferably, but not necessarily identical) having typical dimensions of 30 mm height and 20 mm diameter (38 mm base plate diameter), composed of the same anodized metal as the principle microwave resonator, extend from each end of the microwave resonator 1. The cutoff waveguides 3 and 4 considered as part of the microwave resonator device 1 are critically important for containing the microwave radiation inside the resonator, thereby maintaining high quality, Q, of the resonator (i.e., high amplitudes of the electromagnetic field associated with the microwave signals inside the resonator). The cutoff waveguides 3 and 4 also assist in guiding material 2 through the microwave resonator device 1 during measurement.

Figure 2B:
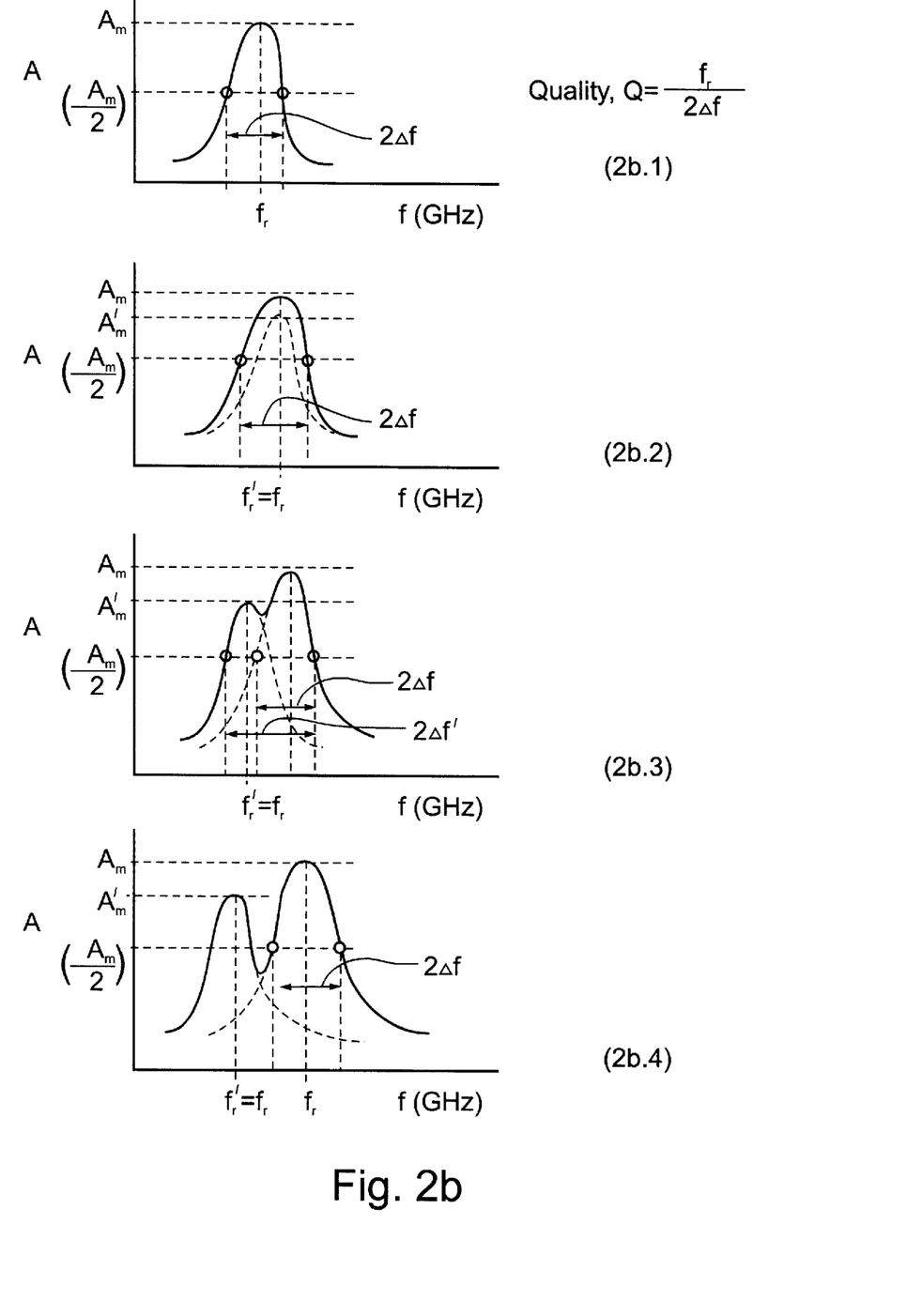
FIG. 2b illustrates the relation of the two principle arrays, determined from measurement inside the microwave resonator (2b.1), and the correction in measurement of resonator quality due to the presence of metal pieces inside the resonator (2b.2, 2b.3, 2b.4)

Inside, and preferably at one end, of the cylindrical microwave resonator 1, are located pieces of metal 16, preferably two in this example, with typical dimensions of length, a=7.3 mm; height, b=6.2 mm; and width, c=1.6 mm, and composed of the same anodized metal as the microwave resonator and waveguides. Explanation of their function is as follows, with reference to FIG. 2b. In FIG. 2b, resonator quality, Q, defined as the ratio of resonance frequency, $f_r$, to twice the resonance frequency full width half amplitude bandwidth, $2\Delta f$, i.e., $Q=f_r/(2\Delta f)$, where the resonance frequency and resonance frequency full width half amplitude bandwidth are measured at maximum amplitude, $A_m$, and half-height of the microwave with maximum amplitude, $A_m/2$, respectively, (2b.1 in FIG. 2b). Inside the cylindrical microwave resonator device 1, during operation under ideal conditions, the type of resonance modes are double-degenerate, whereby each double-degenerate mode of the microwave radiation has two different electromagnetic distributions at the same resonance frequency, $f_r$, i.e., $A_m$ and $A'_m$, (2b.2 in FIG. 2b). For two double-degenerate components, a difference in the amplitude at resonances exists such that two components of the same mode have different couplings with signal input and output ports 7 and 8 (FIG. 2a). In practice, these components exhibit different resonance frequencies, $f_r$ and $f_{r'}$, in addition to different amplitudes, $A_m$ and $A'_m$, respectively, (2b.3 in FIG. 2b), due to structural and/or material imperfections, asymmetries, and/or non-homogeneities of the resonator and/or cutoff waveguides. This phenomenon leads to error in resonance frequency bandwidth received by signal receiver 6, in that $2\Delta f \neq 2\Delta f$, which leads to error in the determination of the quality, Q, of the microwave/resonator device 1, ultimately causing error in measurements of moisture content and in calculations (compensated) of the density of the fibrous material 2. Elimination of this error is accomplished by attaching metal pieces 16 (preferably two, as illustrated in the present invention) to and protruding from the sides of one end of the microwave resonator 1. The metal pieces 16 are positioned inside the resonator at the point of highest electric field (strength) of the component having the lower amplitude. The presence of the metal pieces 16 causes a decrease in the resonance frequency of the component with the smaller amplitude, $A'_m$, resulting in separation of the two resonance curves (2b.4 in FIG. 2b), enabling a correct reading of the resonance frequency full width half amplitude bandwidth, $2\Delta f$, and thus enabling the true quality of the resonator signal to be processed by the CPU 10. Moreover, this correction enables the calculation of highly accurate values of moisture content, and ultimately, density deviation and density, which are to be displayed and/or printed by display unit 11, and used in the automated quality control feedback loop, of the incoming fiber raw material, connected to the CARD machine 13. The preceding corrective design in the cylindrical microwave resonator device 1 is an example only; each microwave resonator configuration requires its own corrective design, based upon the specific material and structural imperfections, asymmetries, and/or non-homogeneities.

In FIG. 2a, centered along the axis of the cylindrical resonator/waveguide device 1 is a cylindrical tube 17, having dimensions of 44 mm height and 16 mm diameter, composed of high purity teflon. The teflon tube 17 guides the fibrous material through the microwave resonator 1 and functions to prevent contamination of the inside of the cavity or walls of the microwave resonator 1, due to the presence of residual fibrous material, thereby eliminating a potential source in reduction of resonator performance.

Measurement and monitoring of temperature and optionally, moisture content, of (production or calibration) fibrous yarn, sliver, or pad material 2 are accomplished by employing a strategically located in-line temperature sensor 9 (in embodiments (a) and (b)), and if needed (as in embodiment (b) only), an optional moisture sensor 15. A thermocouple, thermoresistor, or alternatively, an infrared device can be used as the temperature sensor 9; an infrared device can also be used as the moisture content sensor 15. The temperature and moisture content sensors 9 and 15, respectively, are strategically positioned to monitor, in a real time, continuous or stationary, in-line, and non-invasive mode, the temperature and moisture content of fibrous material 2 entering through the microwave resonator/waveguide device 1. The temperature and moisture content sensor output leads of 9 and 15, respectively, are connected to the central processing unit 10. Measurements of incoming material temperature and moisture content are quite useful compensating calculations of density deviations and density by the CPU 10, and form part of the overall quality control feedback loop for control of temperature and moisture content of raw fibrous material 14 fed into the CARD machine 13.

In the present invention, the relative geometry of the microwave/waveguide resonator device illustrated in FIG. 2a is such to enable the rotation of either the test (production or calibration) fibrous material, the microwave resonator, or the direction of the microwave radiation in the resonator, during real-time, in an in-line, non-invasive mode of density measurement and control. Moreover, the resonator/waveguide configuration in the present invention is well suited for highly accurate, high speed, multi-slice microwave analysis of fibrous material at a downstream (fine tune) stage of the production process.

For calibration and subsequent data analysis purposes, measurements of microwave resonator resonance frequency shifts (i.e., density change) and changes in resonator quality (i.e., moisture content change) are recorded, as a function of temperature (and optionally, moisture content), for the microwave resonator/waveguide device 1 containing air, and standards of fibrous material with varied structural shapes and types characteristics (e.g., yarn, sliver, or pads), in order to sufficiently characterize reference materials with known values of density, moisture content, and structure type as functions of temperature and moisture content. These measurements serve as background data to be subtracted from data of actual measurements of on-line fiber material monitoring and analysis. This subtraction step is critically important in removing the dependency of measurements made by the resonator device of the present invention, on ambient conditions and/or performance levels of electrical equipment and electronic components inside such equipment.

The microwave radiation generator-synthesizer 5 can optionally include a number of features which are designed to maximize the sensitivity of resonance frequency shift (density) and resonator quality (moisture content) measurements of fibrous materials. One such feature is an electric field director which determines the mode of the electric field (strength), established by the microwave source, through input port 7 relative to the test material 2 inside the microwave resonator device 1, such that the mode of the electric field partially determines the magnitudes of frequency shifts and changes in resonator quality (i.e., changes in signal amplitude). Maximum frequency shift and change in resonator quality, due to the presence of test material 2, occur when the electric field of the source microwave radiation is parallel to the test material (not shown). When the electric field is substantially perpendicular to the test material 2, minimum frequency shift and change in resonator quality are obtained. The electric field director determines the direction of the electric field according to data supplied to the CPU 10.

Figure 3:
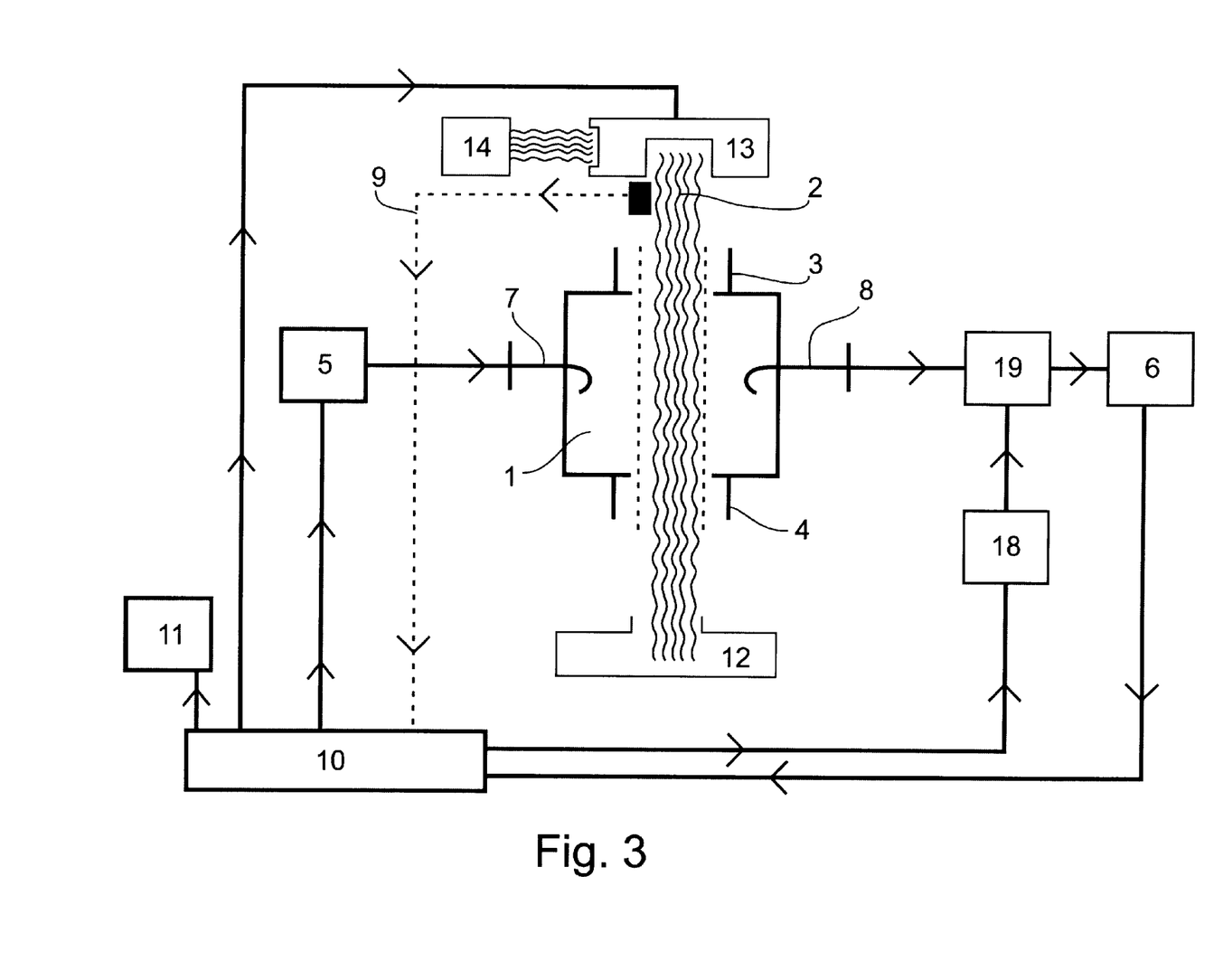
FIG. 3 is a schematic of another embodiment of the present invention, based on the schematic of embodiment (a) in FIG. 1, including and showing the additional components used to enhance dynamic range, sensitivity and accuracy of the quality control feedback.

FIG. 3 is a schematic of another embodiment of the present invention, based on the invention shown in embodiment (a) of FIG. 1, including and showing the additional electronic components 18 and 19 used for enhanced dynamic range, increased sensitivity, and accuracy of signal measurement provided to the CPU 10, which in turn enables better quality control feedback, via signal sent by receiver 6 to the CPU 10, and ultimately to the CARD machine 13, of material processing parameters critical to controlling material density deviation and density, such as material temperature, moisture content, and feed rate of the CARD machine 13. Component 18 is a heterodyne generator-synthesizer, which functions as a local oscillator. Similar to the generator-synthesizer 5, the heterodyne generator-synthesizer generates a sweeping range of frequencies, with each frequency generated at a constant difference from each frequency generated by the generator-synthesizer 5. For example, for generator-synthesizer 5 frequencies of $f_{1i}$, the corresponding frequencies generated by the heterodyne generator-synthesizer could be $f_{2i}$, and so on for all succeeding generated frequencies, whereby, the constant difference between generated frequencies is represented by $f_{1i}-f_{2i}$. The heterodyne generator-synthesizer 18 is connected to and controlled by the CPU 10 such that the differential, or residual, frequency existing between the generator-synthesizer 5 (frequency of the signal entering the material) and the heterodyne generator-synthesizer 18 remains constant, i.e., $f_{1i}-f_{2i}$=constant. Mixer 19 combines the microwave generator-synthesizer signal (passing through signal output port 8) with the heterodyne generator-synthesizer signal 18, and forwards the differential signal to receiver 6. Mixer 19 functions as a type of signal detector, in that it assists in the detection and identification of the unknown resonance frequency shift, due to density deviation in the particular material under analysis. The presence of additional components 18 and 19 in this alternative embodiment of the present invention provides enhanced dynamic range, and increased sensitivity and accuracy in signal detection, and feedback information sent to the CARD machine 13, via the CPU 10.

Figure 4:
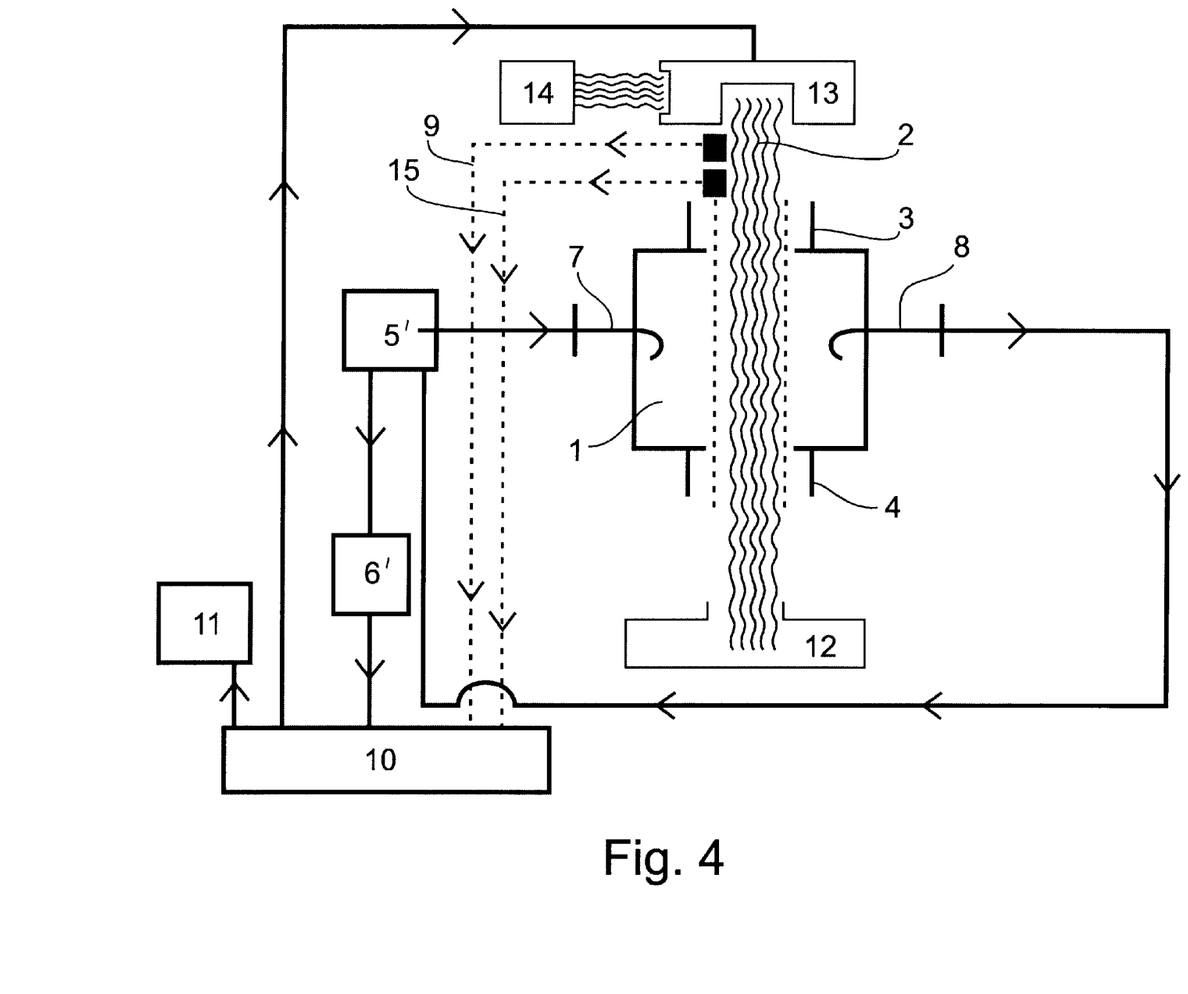
FIG. 4 is a schematic of another embodiment, (b), of the present invention, showing an alternative microwave resonator/waveguide device operating as part of an oscillator.

FIG. 4 is a schematic of another embodiment, embodiment (b), of the present invention, based on the invention shown in embodiment (a) of FIG. 1, including and showing alternative electronic components 5' and 6'. In embodiment (b) of the present invention, the microwave/waveguide resonator device 1 is connected directly to microwave amplifier 5', which in turn sends the signal to a frequency meter 6'. This connection between microwave/waveguide resonator 1 and microwave amplifier 5' represents an alternative, lower cost, similar high accuracy, microwave resonator device, which functions as a closed-loop oscillator, in comparison to the higher cost embodiment (a) shown in FIG. 1, based on the connection between the microwave/waveguide resonator 1 and microwave generator-synthesizer 5. In contrast to embodiment (a), wherein microwaves are generated by the microwave generator-synthesizer 5, in embodiment (b), microwave oscillations are generated as the result of positive feedback between the microwave resonator 1 and the microwave amplifier 5' connected to a DC power source (not shown), along with the presence of fibrous material inside the resonator 1. Frequency meter 6' (which includes a phase shifter and frequency discriminator; not shown) functions as a frequency detector which identifies the oscillator frequency that is 'closest to' the resonance frequency of the microwave resonator 1. Direct connection is made between the frequency meter 6' and the CPU 10, enabling signal measurement and processing, with similar quality control feedback features as provided by embodiment (a) of FIG. 1, i.e., via signal received by the CPU 10, and sent to the CARD machine 13, for adjustment and compensation to the material processing parameters, such as temperature, moisture content, and/or material feed rate. In contrast to embodiment (a) of FIG. 1, embodiment (b) of the present invention of FIG. 4 provides no capability for measurement of the fibrous material moisture content via measuring the quality, Q, of the microwave/waveguide resonator device 1. Instead, a strategically located external moisture content sensor 15, serves as the preferred option for monitoring changes in moisture content of the incoming fibrous material 2, values of which can be used in correcting initial values of density deviations and density calculated by the CPU 10, during real time, in-line operation of the device of this invention.

Figure 5:
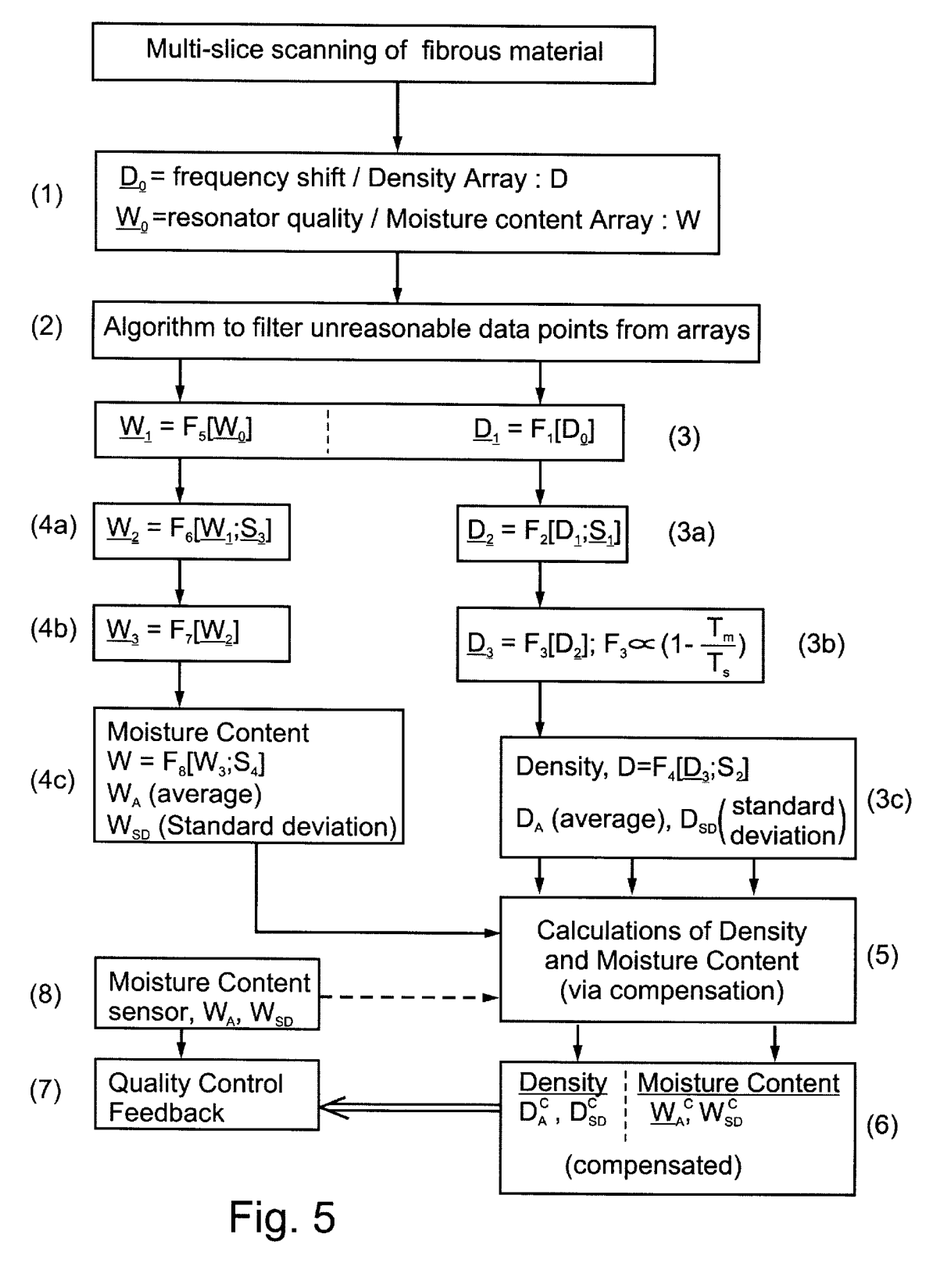
FIG. 5 is a flow chart of the method of calculating density and moisture averages and deviations of fibrous yarn, sliver, or pad material.

FIG. 5 is a flow chart of the method of calculating density (and moisture content) averages and standard deviations of fibrous yarn, sliver, or pad material, for the different embodiments of the present invention (i.e., embodiments (a) and (b), pertaining to FIGS. (1 and 3), and 4, respectively. The overall calculation method used in achieving the objectives of the present invention is based on the evaluation of two arrays (of time samples), D and W, representing an array of resonator resonance frequency shift/density, and an array of resonator quality/moisture content, respectively. Numerical evaluation of the arrays D and W is determined from evaluation of iterative correlation functions, $F_i$ (i.e., $F_1$ through $F_8$), which in turn are functions of resonator frequency shift, resonator quality, material temperature, and four empirically determined structure sensitive (i.e., fiber material shape and type) correlation functions, $S_i$, denoted by $S_1$, $S_2$, $S_3$, and $S_4$. The correlation functions, $F_i$ and $S_i$, represent sets of linear and non-linear functions, each functional form uniquely determined from correlations of calculated density and moisture content values to true, known density and moisture content values, for a variety of fibrous material structural shapes and types. Correlation data are obtained from calibration plots and numerical analysis of density vs resonance frequency shift or moisture content vs resonator quality data, made from data generated during calibration measurements recorded at standard conditions, using reference fibrous materials of known densities, moisture content, temperatures, and of well characterized structure shapes and types. The correlation functions, $F_i$ and $S_i$, provide proper correlations between calculated and known density and moisture content values, according to different fibrous material structural peculiarities or uniqueness, and are critical in achieving high accuracy and reproducibility in calculations of final density and moisture content shown on the display unit and used for input into the quality control feedback loop. Numerical results of these calculations represent averages and standard deviations of density (and optionally, moisture content) of n slices of fibrous material, whereby n is an adjustable parameter proportional to the scan rate of the resonator device.

For embodiment (a), whereby the resonator device operates with a resonator generator-synthesizer (FIGS. 1 and 3), both arrays, D and W are used in calculating density and moisture content averages and standard deviations. The D and W arrays are directly proportional to material density, and moisture content, which in turn are functions of resonator resonance frequency, $f_r$, resonator quality, Q, respectively, material temperature, $T_m$, and all four of the empirically determined structure sensitive correlation functions, $S_i$, ($S_1$, $S_2$, $S_3$, and $S_4$). Moreover, evaluation of array W, providing structural and temperature compensated average and standard deviation values of moisture content, i.e., $W_A$ and $W_{SD}$, are themselves used in compensating and correcting initial average and standard deviation values of density, i.e., $D_A$ and $D_{SD}$, leading to highly accurate moisture content compensated values of density average and standard deviation, i.e., $D^C_A$ and $D^C_{SD}$, per n frequency shift datapoints (i.e., per n slices of analyzed fiber). For embodiment (b), whereby the resonator device operates with the resonator and amplifier as part of an oscillator (FIG. 4), array D is evaluated from the algorithm as in embodiment (a), with the difference that, here array W is evaluated from actual measurements of material moisture content obtained from the external moisture content sensor (since resonator quality is not measured in this embodiment). Here, array D is a function of material temperature $T_m$, and of only two structure sensitive functions, $S_1$ and $S_2$. Measured average and standard deviation values of moisture content, $W^M_A$ and $W^M_{SD}$, are used in compensating initial values of average and standard deviation of density, i.e., $D_A$ and $D_{SD}$, again leading to more accurate moisture content compensated values of density average and standard deviation, i.e., $D^C_A$ and $D^C_{SD}$, per n frequency shift datapoints (i.e., per n slices of analyzed fiber). In either embodiment, calculated values of average and standard deviation of density and moisture content of downstream production material, are subsequently used for real time, in-line, automatic quality control feedback of the upstream manufacturing process of the fibrous yarn, sliver, or pad material.

The first step in the flow chart represents the real time, in-line, continuous or stationary mode, multi-slice scanning of n slices of the fibrous test material using one of the preferred embodiments (a) or (b) (FIGS. 1 and 3, or 4) of the device of the present invention. Multi-slice scanning of the test material, positioned inside the microwave resonator/waveguide device, is performed by continuously transmitting a sweeping set of microwaves of known frequencies into the resonator, and identifying and detecting the affected microwaves by the respective microwave receiver components, i.e., signal receiver 6 or frequency meter 6', according to the corresponding device, i.e., embodiment (a) or (b).

For embodiment (a) of the device, the scanning step provides the necessary raw data for the initial determination of the resonator resonance frequency shift/density array, $D_0$, and the resonator quality array, $W_0$, step (1). Following step (1), an algorithm is used to evaluate, filter and eliminate unreasonable data points from the calculations of initial frequency shift and resonator quality, step (2). The raw frequency data must be filtered in order to eliminate system noise and/or artificial readings of resonance frequency and/or frequency bandwidths. Values of density array, $D_1$, and quality array, $W_1$, are calculated from the appropriate functions, $F_1$, and $F_5$, respectively, following data filtering, step (3). The flow chart now branches into two parts. The right branch shows the steps used in calculating the density of the material, while the left branch shows the steps used in calculating moisture content of the material. For clarity, steps in the right (density) branch, and steps in the left (moisture content) branch, are assigned the numbers 3a–3c, and 4a–4c, respectively. Proceeding with density calculations, the next value of density array, $D_2$, is evaluated from the function, $F_2$, of $D_1$ and $S_1$ (structure correlation function), step (3a). Calculated values of density can now compensated and adjusted for temperature. In step (3b), the next value of density array, $D_3$, is evaluated from the function, $F_3$, of $D_2$ and T, where the dependency of $F_3$ on T is empirically determined, and as an example, is proportional to $(1-T_m/T_s)$, where $T_m$ and $T_s$ are the 'actual' and 'standard' material temperatures, respectively. In step (3c), initial values of the magnitude of the material density array, D, including average density, $D_A$ and density standard deviation, $D_{SD}$, are evaluated from the function, $F_4$, of $D_3$ and $S_2$, another structure sensitive empirical correlation function.

Continuing for the example of embodiment (a) of the device of the present invention, the above initial calculated values of density are to be compensated/corrected for moisture content of the material, determined from resonator quality data according to the left branch of the flow chart. Following elimination of unreasonable values of resonator quality, step (2), and calculation of quality array $W_1$, by using the function, $F_5$ of $W_0$, step (3), the initial value of the moisture content array, $W_2$, is calculated from the function, $F_6$, of $W_1$ and $S_3$, step (4a). The next value of moisture content array, $W_3$, includes compensation and adjustment for temperature. $W_3$ is evaluated from the function, $F_7$, of $W_2$ and T, where the dependency of $F_7$ on T is proportional to $(1-T_m/T_s)$, similar to that of $F_3$, in the above density calculations. In step (4c), the corrected values of the magnitude of material moisture content array, W, including average moisture content, $W_A$ and moisture content standard deviation, $W_{SD}$, are evaluated from the function, $F_8$, of $W_3$ and $S_4$. These values of moisture content are used to compensate the above initial calculated values of density, step (5), in order to obtain final moisture content compensated average and standard deviation values of material density, $D^C_A$ and $D^C_{SD}$, step (6), which are ready for display (FIG. 6) and can be used for feedback control of the fiber based manufacturing process, step (7), (FIGS. 1 and 3, 4, and 7).

For embodiment (b) of the device of the present invention (FIG. 4), resonator quality is not measured; therefore, another method is necessary in order to compensate density calculations for material moisture content. Here, the moisture content array, W, is not calculated according to the left branch of the flow chart, but instead, is evaluated from actual measurements of material moisture content performed by the external moisture content sensor, step (8), whereby, measured average and standard deviation moisture content, i.e., $W^M_A$ and $W^M_{SD}$, data are compiled by the CPU 10 for use as needed. Initial values of density, $D_A$ and $D_{SD}$ are calculated as before in embodiment (a), according to the right branch of the flow chart. The measured values of moisture content are then used to compensate the above initial calculated values of density, step (5), in order to obtain final compensated average and standard deviation values of material density, $D^C_A$ and $D^C_{SD}$, step (6), which are ready for display (FIG. 6) and can also be used for feedback control of the fiber based manufacturing process, step (7), (FIGS. 1 and 3, and 4).

Figure 6:
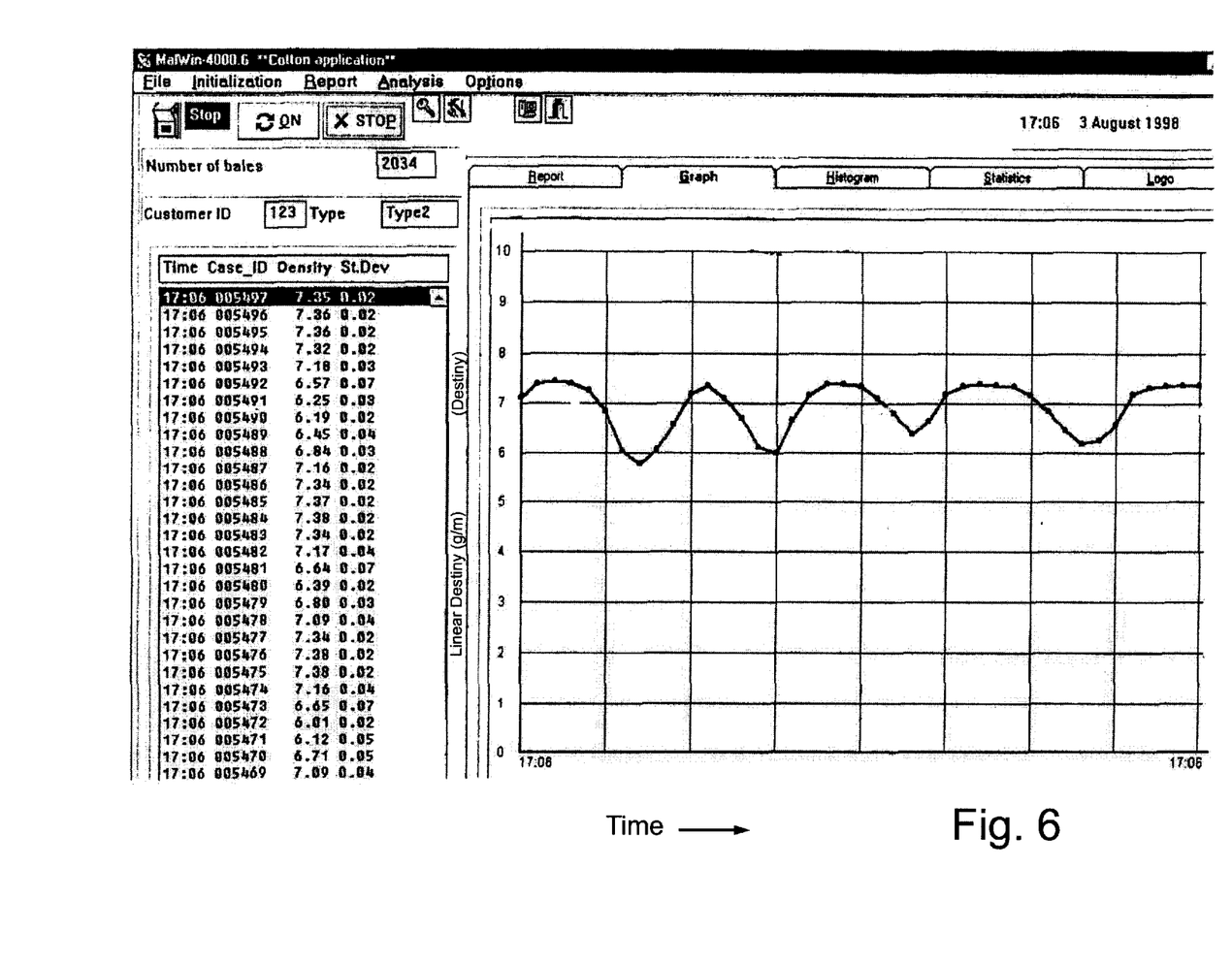
FIG. 6 is a sample display showing (linear) density average and standard deviation as functions of time, based on typical results obtained from measurements using embodiment (a) of the device (FIG. 1), performed on a continuous fibrous sliver, as part of an actual fiber based production process.

FIG. 6 is a sample display showing numerical and graphical values of compensated fiber (linear) density average and standard deviation, $D^C_A$ and $D^C_{SD}$, as functions of time, based on typical results obtained from measurements of the device of embodiment (a), (FIG. 1), performed on a continuous fibrous sliver, as part of a tampon production process. Information of this sample printout is readily displayed, in a real time, in-line, continuous mode of operation, on the computerized display device 11, (FIGS. 1, 3, or 4), as typical of the different embodiments of the present invention.

Figure 7:
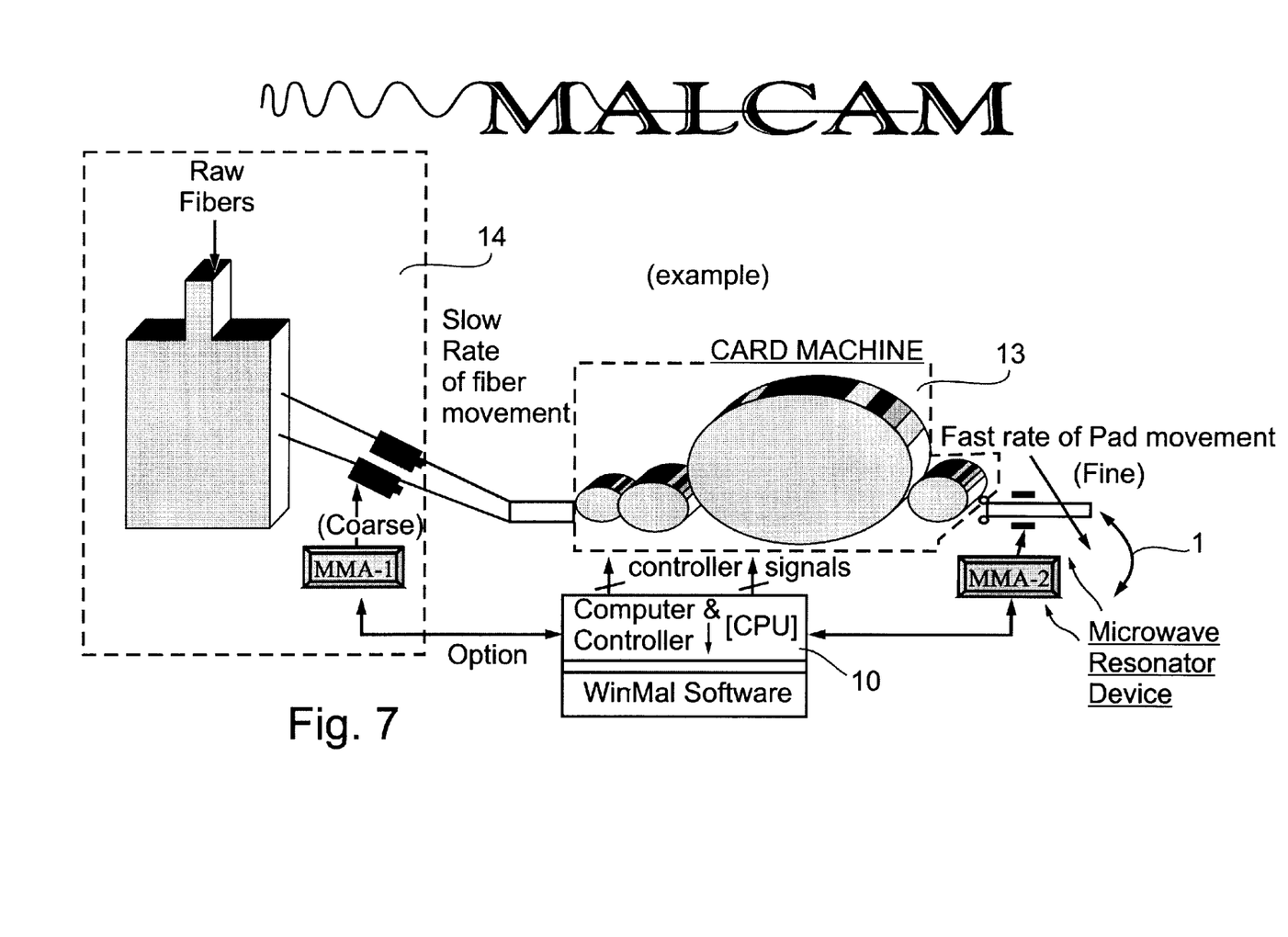
FIG. 7 is a diagram of an example of an overall fiber based manufacturing process, highlighting the physical locations of the device of the present invention (i.e., MMA-2), relative to that of the device of a prior art invention (i.e., MMA-1).

FIG. 7 is a diagram of an example of an overall fiber based manufacturing process, highlighting the preferred physical location of the resonator device 1 of the present invention (i.e., MMA-2), relative to that of the moisture measuring device of a prior art invention (i.e., MMA-1). In FIG. 7, unprocessed, relatively high density (e.g., 10–15 kg per cubic meter), fibrous raw material 14 is fed into the CARD machine 13. The CARD machine functions to separate and decrease the density of fibers at an upstream stage, in order to enable the programmed mixing of the fibers at a downstream production stage. Fibrous material exiting the CARD machine 13, is in a lower density form (e.g., 4–12 grams per meter, linear density) of yarn, slivers, or pad, and enters the in-line microwave/waveguide resonator device 1. Fibrous material exiting the microwave/waveguide resonator device 1 continues into further downstream fiber processing machines, en route to finished fiber based product. This location of the microwave resonator device 1 is well suited, in a complementary way, to serve as part of fine tune control of semi-processed fibrous material, relative to the upstream location of an optional moisture content monitor (coarse control) of unprocessed fibrous raw material.

It will be appreciated that the above descriptions are intended only to serve as examples, and that many other embodiments are possible within the spirit and the scope of the present invention.

What is claimed is:

1. A method for continuously determining the density of a fibrous material, comprising the steps of:
   (a) continuously guiding the fibrous material through and parallel to height of a cylindrical microwave resonator having a microwave resonance frequency, said cylindrical microwave resonator includes:
      (i) an electrically conductive housing defining a cylindrical cavity having an input end and an output end;
      (ii) a plastic cylindrical tube spanning inside said cylindrical cavity from said input end to said output end, wherein ratio of length of said cylindrical cavity to length of said plastic cylindrical tube is about one, and wherein ratio of diameter of said cylindrical cavity to diameter of said plastic cylindrical tube is between about two and three to one, for said continuously guiding the fibrous material through and parallel to height of said cylindrical microwave resonator and for preventing contamination by residual fibrous material inside said cylindrical cavity; and
      (iii) a mechanism for measuring a shift in said resonance frequency caused by a presence of the fibrous material inside said cylindrical cavity;
   (b) measuring said shift in said resonance frequency caused by said presence of the fibrous material inside said cylindrical cavity; and
   (c) inferring the density of the fibrous material from said shift.

2. The method of claim 1, wherein said cylindrical microwave resonator has a resonator quality, the method further comprising the step of:
   (d) measuring a change in said resonator quality caused by the fibrous material, wherein said inferring the density of the fibrous material is based on both said shift of said resonance frequency and on said change in said resonator quality.

3. The method of claim 1, further comprising the step of:
   (d) measuring a moisture content of the fibrous material, wherein said inferring of the density of the fibrous material is based on both said shift of said resonance frequency and on said moisture content of the fibrous material.

4. The method of claim 1, further comprising the step of:
   (d) measuring a temperature of the fibrous material, wherein said inferring the density of the fibrous material is based on both said shift of resonance frequency and on said temperature of the fibrous material.

5. The method of claim 1, further comprising the step of:
   (d) measuring a structural characteristic of the fibrous material, wherein said inferring the density of the fibrous material is based on both said shift of resonance frequency and on said structural characteristic of the fibrous material.

6. The method of claim 1, wherein said plastic cylindrical tube includes a fluorocarbon polymer.

7. The method of claim 1, wherein said cylindrical cavity has two substantially identical microwave resonance frequencies with respect to two degenerate modes of microwave radiation, said cylindrical microwave resonator further includes:
   (iv) a mechanism for separating degeneracy of said two degenerate modes, so that said cylindrical cavity has two separate microwave resonance frequencies with respect to said two degenerate modes; and
   (v) a mechanism for measuring a shift in one of said separate microwave resonance frequencies caused by said presence of the fibrous material inside said cylindrical cavity.

8. The method of claim 7, wherein said mechanism for said separating said degeneracy includes at least one piece of metal located entirely inside said cylindrical cavity of said cylindrical microwave resonator.

9. The method of claim 8, wherein ratio of volume of said cylindrical cavity to volume of each said at least one piece of metal is about seven-hundred to one.

10. The method of claim 7, wherein said mechanism for said separating said degeneracy includes at least two pieces of metal located entirely inside and substantially at one end of said cylindrical cavity of said cylindrical microwave resonator.

11. The method of claim 10, wherein ratio of volume of said cylindrical cavity to volume of each said at least two pieces of metal is about seven-hundred to one.

12. A method for continuously determining the density of a fibrous material, comprising the steps of:
   (a) continuously guiding the fibrous material through and parallel to height of a cylindrical microwave resonator having a microwave resonance frequency, said cylindrical microwave resonator includes:
      (i) an electrically conductive housing defining a cylindrical cavity having two substantially identical microwave resonance frequencies with respect to two degenerate modes of microwave radiation, said cylindrical cavity having an input end and an output end;

(ii) a mechanism for separating degeneracy of said two degenerate modes, so that said cylindrical cavity has two separate microwave resonance frequencies with respect to said two degenerate modes, said mechanism for said separating said degeneracy is at least two pieces of metal located entirely inside, attached to and internally protruding from sides of one end of said cylindrical cavity, whereby said metal pieces cause a decrease in said microwave resonance frequency of one of said two degenerate modes with smaller amplitude of said microwave radiation; and (iii) a mechanism for measuring a shift in one of said separate microwave resonance frequencies caused by a presence of the fibrous material inside said cylindrical cavity;

(b) measuring said shift in said one of said separate resonance frequencies caused by said presence of the fibrous material inside said cylindrical cavity; and (c) inferring the density of the fibrous material from said shift.

13. The method of claim 12, wherein said cylindrical microwave resonator has a resonator quality, the method further comprising the step of:

(d) measuring a change in said resonator quality caused by the fibrous material, wherein said inferring the density of the fibrous material is based on both said shift of said resonance frequency and on said change in said resonator quality.

14. The method of claim 12, further comprising the step of:

(d) measuring a moisture content of the fibrous material, wherein said inferring of the density of the fibrous material is based on both said shift of said resonance frequency and on said moisture content of the fibrous material.

15. The method of claim 12, further comprising the step of:

(d) measuring a temperature of the fibrous material, wherein said inferring the density of the fibrous material is based on both said shift of resonance frequency and on said temperature of the fibrous material.

16. The method of claim 12, further comprising the step of:

(d) measuring a structural characteristic of the fibrous material, wherein said inferring the density of the fibrous material is based on both said shift of resonance frequency and on said structural characteristic of the fibrous material.

17. The method of claim 12, wherein ratio of volume of said cylindrical cavity to volume of each said at least two pieces of metal is about seven-hundred to one.

18. The method of claim 12, wherein said cylindrical microwave resonator further includes:

(iv) a plastic tube spanning inside said cylindrical cavity from said input end to said output end, for said continuously guiding the fibrous material through and parallel to height of said cylindrical microwave resonator and for preventing contamination by residual fibrous material inside said cylindrical cavity.

19. The method of claim 18, wherein said plastic tube includes a fluorocarbon polymer.

20. The method of claim 18, wherein ratio of length of said cylindrical cavity to length of said plastic tube is about one, and wherein ratio of diameter of said cylindrical cavity to diameter of said plastic tube is about two and four-tenths to one.

21. A device for continuously determining the density of a fibrous material, comprising:

(a) a cylindrical microwave resonator having a microwave resonance frequency, for continuously guiding the fibrous material through and parallel to height of said cylindrical microwave resonator, said cylindrical microwave resonator includes:

(i) an electrically conductive housing defining a cylindrical cavity having an input end and an output end; and (ii) a plastic cylindrical tube spanning inside said cylindrical cavity from said input end to said output end, wherein ratio of length of said cylindrical cavity to length of said plastic cylindrical tube is about one, and wherein ratio of diameter of said cylindrical cavity to diameter of said plastic cylindrical tube is between about two and three to one, for said continuously guiding the fibrous material through and parallel to height of said cylindrical microwave resonator and for preventing contamination by residual fibrous material inside said cylindrical cavity; and (b) a mechanism for measuring a shift in said resonance frequency caused by a presence of the fibrous material inside said cylindrical cavity; and (c) a mechanism for generating microwave radiation.

22. The device of claim 21, wherein said cylindrical microwave resonator further includes:

(iii) a first cutoff waveguide adjacent said input end; and (iv) a second cutoff waveguide adjacent said output end.

23. The device of claim 21, wherein said cylindrical microwave resonator has a resonator quality, the device further comprising:

(d) a mechanism for measuring a change in said resonator quality caused by said presence of the fibrous material inside said cylindrical cavity.

24. The device of claim 21, further comprising:

(d) at least one fibrous material parametric sensor selected from the group consisting of a fibrous material temperature sensor and a fibrous material moisture content sensor.

25. The device of claim 21, wherein said mechanism for said generating said microwave radiation includes a device selected from the group consisting of a broadband generator-synthesizer and an amplifier.

26. The device of claim 21, wherein said plastic cylindrical tube includes a fluorocarbon polymer.

27. The device of claim 21, wherein said cylindrical cavity has two substantially identical microwave resonance frequencies with respect to two degenerate modes of said microwave radiation, said cylindrical microwave resonator further includes:

(iii) a mechanism for separating degeneracy of said two degenerate modes, so that said cylindrical cavity has two separate microwave resonance frequencies with respect to said two degenerate modes.

28. The device of claim 27, further comprising:

(d) a mechanism for measuring a shift in one of said separate microwave resonance frequencies caused by said presence of the fibrous material inside said cylindrical cavity.

29. The device of claim 27, wherein said mechanism for said separating said degeneracy includes at least one piece of metal located entirely inside said cylindrical cavity of said cylindrical microwave resonator.

30. The device of claim 29, wherein ratio of volume of said cylindrical cavity to volume of each said at least one piece of metal is about seven-hundred to one.

31. The device of claim 27, wherein said mechanism for said separating said degeneracy includes at least two pieces of metal located entirely inside and substantially at one end of said cylindrical cavity of said cylindrical microwave resonator.

32. The device of claim 31, wherein ratio of volume of said cylindrical cavity to volume of each said at least two pieces of metal is about seven-hundred to one.

33. A device for continuously determining the density of a fibrous material, comprising:
 (a) a cylindrical microwave resonator having a microwave resonance frequency, for continuously guiding the fibrous material through and parallel to height of said cylindrical microwave resonator, said cylindrical microwave resonator includes:
  (i) an electrically conductive housing defining a cylindrical cavity having two substantially identical microwave resonance frequencies with respect to two degenerate modes of microwave radiation, said cylindrical cavity having an input end and an output end; and
  (ii) a mechanism for separating degeneracy of said two degenerate modes, so that said cylindrical cavity has two separate microwave resonance frequencies with respect to said two degenerate modes, said mechanism for said separating said degeneracy is at least two pieces of metal located entirely inside, attached to and internally protruding from sides of one end of said cylindrical cavity, whereby said metal pieces cause a decrease in said microwave resonance frequency of one of said two degenerate modes with smaller amplitude of said microwave radiation; and
 (b) a mechanism for measuring a shift in one of said separate microwave resonance frequencies caused by a presence of the fibrous material inside said cylindrical cavity; and
 (c) a mechanism for generating microwave radiation.

34. The device of claim 33, wherein said cylindrical microwave resonator further includes:
  (iii) a first cutoff waveguide adjacent said input end; and
  (iv) a second cutoff waveguide adjacent said output end.

35. The device of claim 33, wherein said cylindrical microwave resonator has a resonator quality, the device further comprising:
 (d) a mechanism for measuring a change in said resonator quality caused by said presence of the fibrous material inside said cylindrical cavity.

36. The device of claim 33, further comprising:
 (d) at least one fibrous material parametric sensor selected from the group consisting of a fibrous material temperature sensor and a fibrous material moisture content sensor.

37. The device of claim 33, wherein said mechanism for said generating said microwave radiation includes a device selected from the group consisting of a broadband generator-synthesizer and an amplifier.

38. The device of claim 33, wherein said cylindrical microwave resonator further includes:
  (iii) a plastic tube spanning inside said cylindrical cavity from said input end to said output end, for said continuously guiding the fibrous material through and parallel to height of said cylindrical microwave resonator and for preventing contamination by residual fibrous material inside said cylindrical cavity.

39. The device of claim 38, wherein said plastic tube includes a fluorocarbon polymer.

40. The device of claim 38, wherein ratio of length of said cylindrical cavity to length of said plastic tube is about one, and wherein ratio of diameter of said cylindrical cavity to diameter of said plastic tube is about two and four-tenths to one.

* * * * *